(12) United States Patent
Lin et al.

(10) Patent No.: US 11,013,716 B2
(45) Date of Patent: May 25, 2021

(54) METHOD FOR PROVIDING AN INCREASED EXPRESSION OF TELOMERASE, BRAIN-DERIVED NEUROTROPHIC FACTOR, STROMAL CELL-DERIVED FACTOR-1, CXC CHEMOKINE RECEPTOR 4, AND/OR IMMUNE REGULATORY FACTOR OF STEM CELL

(71) Applicant: HAWKING BIOLOGICAL TECHNOLOGY CO., LTD, New Taipei (TW)

(72) Inventors: Shinn-Zong Lin, New Taipei (TW); Horng-Jyh Harn, New Taipei (TW); Tzyy-Wen Chiou, New Taipei (TW); Kuo-Wei Hsueh, New Taipei (TW); Mao-Hsuan Huang, New Taipei (TW)

(73) Assignee: HAWKING BIOLOGICAL TECHNOLOGY CO., LTD., New Taipei (TW)

( * ) Notice: Subject to any disclaimer, the term of this patent is extended or adjusted under 35 U.S.C. 154(b) by 0 days.

(21) Appl. No.: 15/188,691

(22) Filed: Jun. 21, 2016

(65) Prior Publication Data
US 2016/0324826 A1 Nov. 10, 2016

Related U.S. Application Data

(62) Division of application No. 14/199,250, filed on Mar. 6, 2014, now abandoned.
(Continued)

(30) Foreign Application Priority Data

Jan. 29, 2014 (TW) ................. 103103485

(51) Int. Cl.
*A61K 35/28* (2015.01)
*A61K 31/365* (2006.01)
(Continued)

(52) U.S. Cl.
CPC .......... *A61K 31/365* (2013.01); *A61K 9/0019* (2013.01); *A61K 9/0085* (2013.01);
(Continued)

(58) Field of Classification Search
CPC .. A61K 9/0019; A61K 9/0085; A61K 31/365; A61K 31/7048; A61K 35/28;
(Continued)

(56) References Cited

U.S. PATENT DOCUMENTS 8,729,026 B2 * 5/2014 Lin ...................... A61K 31/365
514/17.9
2011/0311496 A1 12/2011 Pittenger
(Continued)

FOREIGN PATENT DOCUMENTS

CN 102014936 4/2011
CN 102397272 4/2012
(Continued)

OTHER PUBLICATIONS

Yi Li and Michael Chopp, Marrow stromal cell transplantation in stroke and traumatic brain injury, 2009, Neurosci. Lett., vol. 456(3), pp. 120-123 (Year: 2009).*
(Continued)

*Primary Examiner* — Michelle F. Paguio Frising
*Assistant Examiner* — Trent R Clarke
(74) *Attorney, Agent, or Firm* — Ping Wang; Morris, Manning & Martin LLP

(57) ABSTRACT

A method for providing an increased expression of at least one of telomerase, brain-derived neurotrophic factor (BDNF), stromal cell-derived factor-1 (SDF1), CXC chemokine receptor 4 (CXCR4), and an immune regulatory factor of a stem cell in a subject is provided. The method comprises
(Continued)

simultaneously or separately administering to the subject an effective amount of (a) a phthalide and (b) a stem cell.

3 Claims, 7 Drawing Sheets
(5 of 7 Drawing Sheet(s) Filed in Color)
Specification includes a Sequence Listing.

Related U.S. Application Data

(60) Provisional application No. 61/777,127, filed on Mar. 12, 2013.

(51) Int. Cl.

| | | |
|---|---|---|
| *A61K 35/35* | (2015.01) | |
| *A61K 35/50* | (2015.01) | |
| *A61K 35/51* | (2015.01) | |
| *A61K 35/545* | (2015.01) | |
| *A61K 31/7048* | (2006.01) | |
| *A61K 9/00* | (2006.01) | |

(52) U.S. Cl.
CPC .......... *A61K 31/7048* (2013.01); *A61K 35/28* (2013.01); *A61K 35/35* (2013.01); *A61K 35/50* (2013.01); *A61K 35/51* (2013.01); *A61K 35/545* (2013.01)

(58) Field of Classification Search
CPC ........ A61K 35/35; A61K 35/50; A61K 35/51; A61K 35/545
See application file for complete search history.

(56) References Cited

U.S. PATENT DOCUMENTS

| | | |
|---|---|---|
| 2013/0158108 A1 | 6/2013 | Chiou |
| 2014/0045765 A1* | 2/2014 | Lin .................... A61K 31/365 514/17.9 |

FOREIGN PATENT DOCUMENTS

| | | | |
|---|---|---|---|
| WO | 2006125651 | 11/2006 | |
| WO | 2009/111030 | 9/2009 | |
| WO | WO-2010110755 A1 * | 9/2010 | ........... A61K 36/537 |

OTHER PUBLICATIONS

J. Chen, Y. Li, M. Katakowski, X. Chen, L. Wang, D. Lu, M. Lu, S. C. Gautam & M. Chopp, Intravenous Bone Marrow Stromal Cell Therapy Reduces Apoptosis and Promotes Endogenous Cell Proliferation After Stroke in Female Rat, 2003, Journal of Neuroscience Research, vol. 73, pp. 778-786 (Year: 2003).*
Kwang S. Kim, Hong J. Lee, Jin An, Yun B. Kim, Jung Chan Ra, Inja Lim and Seung U. Kim, Transplantation of Human Adipose Tissue-Derived Stem Cells Delays Clinical Onset and Prolongs Life Span in ALS Mouse Model, 2014, Cell Transplantation, vol. 23, pp. 1585-1597 (Year: 2014).*
Zhang, G. L., "The effects of NBP on the lifespan and CDK5 P35 expression in the mice model of ALS", Hebei Medical University, 2012.
Qing, L. et al., "Research progress in stem cell transplantation for treating amyotrophic lateral sclerosis", Journal of Clinical Rehabilitative Tissue Engineering Research, 2009, vol. 13(10), pp. 1942-1946.
Liu, S-P. et al., "n-Butylidenephthalide (BP) Maintains Stem Cell Pluripotency by Activating Jak2/Stat3 Pathway and Increases the Efficiency of iPS Cells Generation", PLOS ONE, 2012, vol. 7(9), pp. 1-12.
The effects of NBP on the lifespan and CDK5 P35 expression in the mice model of ALS, 2012.
Yan, R. et al., "Pharmacokinetics and Metabolism of Ligustilide, a Major Bioactive Component in Rhizoma Chuanxiong, in the Rat", The American Society for Pharmacology and Experimental Therapeutics, 2008, vol. 36(2), pp. 400-408.
Xiaoli, L. et al., "Experimental study of the effects of butylphthalide on focal cerebral ischemic tolerance induced by ischemic preconditioning", Journal of Gerontology, 2012, 31 vol. 6, pp. 529-531.
Park, D et al., "Human adipose tissue-derived mesenchymal stem cells improve cognitive function and physical activity in ageing mice", J Neurosci Res., May 2013; vol. 91(5), pp. 660-670.
Garbuzova-Davis, S et al., "Human Umbilical Cord Blood Treatment in a Mouse Model of ALS: Optimization of Cell Dose", PLoS ONE, Jun. 2008, vol. 3(6), pp. 1-14.
Kohman, R et al., "Neurogenesis, Inflammation and Behavior", Brain Behav Immun., Jan. 2013, vol. 27, pp. 22-32.
Zhao, D.C. et al., "Bone marrow-derived mesenchymal stem cells protect against experimental liver fibrosis in rats", World J Gastroenterol., Jun. 2005, vol. 11(22), pp. 3431-3440.

* cited by examiner

FIGURES

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: BDNF primer- Forward Sequence

<400> SEQUENCE: 1
gtgtgcgaca gcattagcca gtgg          24

<210> SEQ ID NO 2
<211> LENGTH: 26
<212> TYPE: DNA

```
<213> ORGANISM: Artificial Sequence
<220> FEATURE:
<223> OTHER INFORMATION: BDNF primer- Reverse Sequence

<400> SEQUENCE: 2
cacatacatg aaactggtaa ttctcc                                      26

<210> SEQ ID NO 3
<211> LENGTH: 21
<212> TYPE: DNA
<213> ORGANISM: Artificial Sequence
<220> FEATURE:
<223> OTHER INFORMATION: SDF1 primer- Forward Sequence

<400> SEQUENCE: 3
atgaacgcca aggtcgtggt c                                           21

<210> SEQ ID NO 4
<211> LENGTH: 26
<212> TYPE: DNA
<213> ORGANISM: Artificial Sequence
<220> FEATURE:
<223> OTHER INFORMATION: SDF1 primer- Reverse Sequence

<400> SEQUENCE: 4
tcatggacct ctttcgaaat ttgttc                                      26

<210> SEQ ID NO 5
<211> LENGTH: 20
<212> TYPE: DNA
<213> ORGANISM: Artificial Sequence
<220> FEATURE:
<223> OTHER INFORMATION: CXCR4 primer- Forward Sequence

<400> SEQUENCE: 5
ggccctcaag accacagtca                                             20

<210> SEQ ID NO 6
<211> LENGTH: 23
<212> TYPE: DNA
<213> ORGANISM: Artificial Sequence
<220> FEATURE:
<223> OTHER INFORMATION: CXCR4 primer- Reverse Sequence

<400> SEQUENCE: 6
gaagttcaaa agtgaggtcg att                                         23

<210> SEQ ID NO 7
<211> LENGTH: 20
<212> TYPE: DNA
<213> ORGANISM: Artificial Sequence
<220> FEATURE:
<223> OTHER INFORMATION: interleukin 6 primer- Forward Sequence

<400> SEQUENCE: 7
tgccagcctg ctgacgaagc                                             20

<210> SEQ ID NO 8
<211> LENGTH: 20
<212> TYPE: DNA
<213> ORGANISM: Artificial Sequence
<220> FEATURE:
<223> OTHER INFORMATION: interleukin 6 primer- Reverse Sequence

<400> SEQUENCE: 8
tctgtgccca gtggacaggt                                             20
```

```
<210> SEQ ID NO 9
<211> LENGTH: 20
<212> TYPE: DNA
<213> ORGANISM: Artificial Sequence
<220> FEATURE:
<223> OTHER INFORMATION: interleukin 8 primer- Forward Sequence

<400> SEQUENCE: 9
gctggccgtg gctctcttgg                                            20

<210> SEQ ID NO 10
<211> LENGTH: 20
<212> TYPE: DNA
<213> ORGANISM: Artificial Sequence
<220> FEATURE:
<223> OTHER INFORMATION: interleukin 8 primer- Reverse Sequence

<400> SEQUENCE: 10
tccacaaccc tctgcaccca                                            20
```

METHOD FOR PROVIDING AN INCREASED EXPRESSION OF TELOMERASE, BRAIN-DERIVED NEUROTROPHIC FACTOR, STROMAL CELL-DERIVED FACTOR-1, CXC CHEMOKINE RECEPTOR 4, AND/OR IMMUNE REGULATORY FACTOR OF STEM CELL

CROSS-REFERENCES TO RELATED APPLICATIONS

The present application is a divisional application of U.S. patent application Ser. No. 14/199,250, filed on Mar. 6, 2014, the entire contents of which are incorporated herein by reference. The Ser. No. 14/199,250 application claimed the benefit of the date of the earlier filed Taiwanese Patent Application No. 103103485 filed on Jan. 29, 2014 and U.S. Provisional Application Ser. No. 61/777,127 filed on Mar. 12, 2013, priority to which are also claimed herein, and the contents of which are also incorporated herein by reference herein.

BACKGROUND OF THE INVENTION

1. Field of the Invention

The present invention relates to a method for providing an increased expression of at least one of telomerase, brain-derived neurotrophic factor (BDNF), stromal cell-derived factor-1 (SDF1), CXC chemokine receptor 4 (CXCR4), and an immune regulatory factor of a stem cell in a subject, and relates to a method for treating motor neuron degenerative diseases and/or delaying the onset of motor neuron degenerative diseases.

2. Descriptions of the Related Art

A neuron, also known as a nerve cell, is one of the structural and functional units of the nervous system of an organism. Neurons can transmit messages to other cells by chemical and electrical signals. Neurons can vary in shape and size, and the diameters of neurons may range from about 4 μm to about 100 μm. The structure of a neuron can be roughly divided into three parts: a cell body, dendrites, and an axon, wherein the dendrites can transmit signals into the cell body, and the axon can transmit signals out from the cell body.

Neurons can be classified into three types depending on their functions and signal transmission directions: sensory neurons, motor neurons and interneurons, wherein a motor neuron is a nerve cell controlling the body activities of an organism. In general, motor neurons in the brain are known as upper motor neurons, while motor neurons in the brain stem and the spinal cord are known as lower motor neurons. Malfunctions caused by the degeneration of motor neurons may result in motor neuron degenerative diseases, such as amyotrophic lateral sclerosis (ALS), myasthenia gravis, myasthenia, muscular atrophy, muscular dystrophy, multiple sclerosis, multiple-system atrophy, spinal muscular dystrophy, etc. Patients suffering from the aforesaid motor neuron degenerative diseases will gradually show symptoms such as muscle weakness, atrophy, trembling, cramping rigidity, which may lead to difficulty speaking, difficulty swallowing, respiratory failure, etc.

The real cause of motor neuron degenerative diseases is still uncertain to date. However, research has shown that the possible causes of the diseases include neuronal death caused by over expression of autophagy stimulated by the accumulation of superoxide anions, autoimmune disorder, excessive neuronal excitation (e.g., excessive accumulation of glutamates), excessive oxidation of neuron, heredity, etc. Medicines presently used in clinic to treat motor neuron degenerative diseases include glutamate antagonists such as Riluzole, antioxidants such as vitamin E, neurotrophic factors, immune modulators, etc. However, the aforesaid medicines usually do not have significant therapeutic effects or may only lengthen the life of the patients for 3 to 6 months.

In addition, researches have found that a stem cell can differentiate into a neural cell, which brings hope for the treatment of nervous system diseases, such as Parkinson's disease, stroke, brain injury, and spinal cord injury. For example, researches have found that a stem cell can pass through the blood brain barrier via intravenous injection (i.e., intravenous transplantation) to alleviate neurodegeneration caused by aging and can repair and reconstruct the damaged cerebrovascular to maintain the normalization and/or youthfulness of cranial nerves. Furthermore, researches revealed that the stem cell therapy has shown evident treating efficacy on the patients with brain atrophy and Alzheimer's disease. However, the aforementioned researches also showed that the stem cell therapy does not have significant therapeutic effect on motor neuron degenerative diseases or may only provide a limited effect, such as prolonging the longevity of the mice with amyotrophic lateral sclerosis to about 140 days (see "Garbuzova-Davis et al., Human umbilical cord blood treatment in a mouse model of ALS: optimization of cell dose, 2008," which is entirely incorporated hereinto by reference). Therefore, there is still a need for an approach to treat motor neuron degenerative diseases and/or delay the onset of motor neuron degenerative diseases.

The inventors of the present invention found that a combined use of a phthalide and a stem cell in a subject can increase the expression of telomerase, brain-derived neurotrophic factor (BDNF), stromal cell-derived factor-1 (SDF1), CXC chemokine receptor 4 (CXCR4), and an immune regulatory factor of a stem cell (such as interleukin 6 (IL-6) and interleukin 8 (IL-8)) of the stem cell in the subject. A combination of a phthalide and a stem cell can provides an effect on treating motor neuron degenerative diseases and/or delaying the onset of motor neuron degenerative diseases.

SUMMARY OF THE INVENTION

An objective of the present invention is to provide a method for providing an increased expression of at least one of telomerase, brain-derived neurotrophic factor (BDNF), stromal cell-derived factor-1 (SDF1), CXC chemokine receptor 4 (CXCR4), and an immune regulatory factor of a stem cell in a subject, comprising simultaneously or separately administering to the subject an effective amount of (a) a phthalide and (b) a stem cell, wherein said increased expression is increased in comparison with a corresponding expression of the effective amount of the stem cell in the subject without being administered with a phthalide.

Another objective of the present invention is to provide a kit, comprising: a first composition, comprising a phthalide; and a second composition, comprising a stem cell; wherein the first composition and the second composition are to be administered to a subject in need simultaneously or separately.

Yet another objective of the present invention is to provide a method for treating a motor neuron degenerative disease and/or delaying the onset of a motor neuron degenerative disease in a subject, comprising administering to the subject an effective amount of a metabolic precursor of a phthalide, wherein the metabolic precursor is 3-butylidene-4,5-dihydrophthalide (ligustilide).

The detailed technology and the preferred embodiments implemented for the present invention will be described in the following paragraphs for people skilled in the field to appreciate the features of the claimed invention.

BRIEF DESCRIPTION OF THE DRAWINGS

The patent application contains at least one drawing executed in color. Copies of this patent document with color drawing(s) will be provided by the Office upon request and payment of the necessary fee.

FIGS. 1A-1C show the metabolism of n-butylidenephthalide (BP) in a organism, wherein FIG. 1A is a mass spectrum of a mixture of BP and human hepatic microsomes analyzed by LC-MS/MS, FIG. 1B is a metabolic profile showing the phase I metabolism of BP in an organism, and FIG. 1C is a metabolic profile showing the phase II metabolism of BP in an organism.

FIGS. 6A-6C show the protein expression levels of SOD1-G93A transgenic mice treated with a combination of BP and stem cells, wherein FIG. 6A is an immunohistochemical staining picture obtained by using an anti-human mitochondria antibody, FIG. 6B is an immunohistochemical staining picture obtained by using an anti-human BDNF antibody, and FIG. 6C is an immunohistochemical staining picture obtained by using an anti-human CXCR4 antibody.

DETAILED DESCRIPTION OF THE INVENTION

Figure 1A:
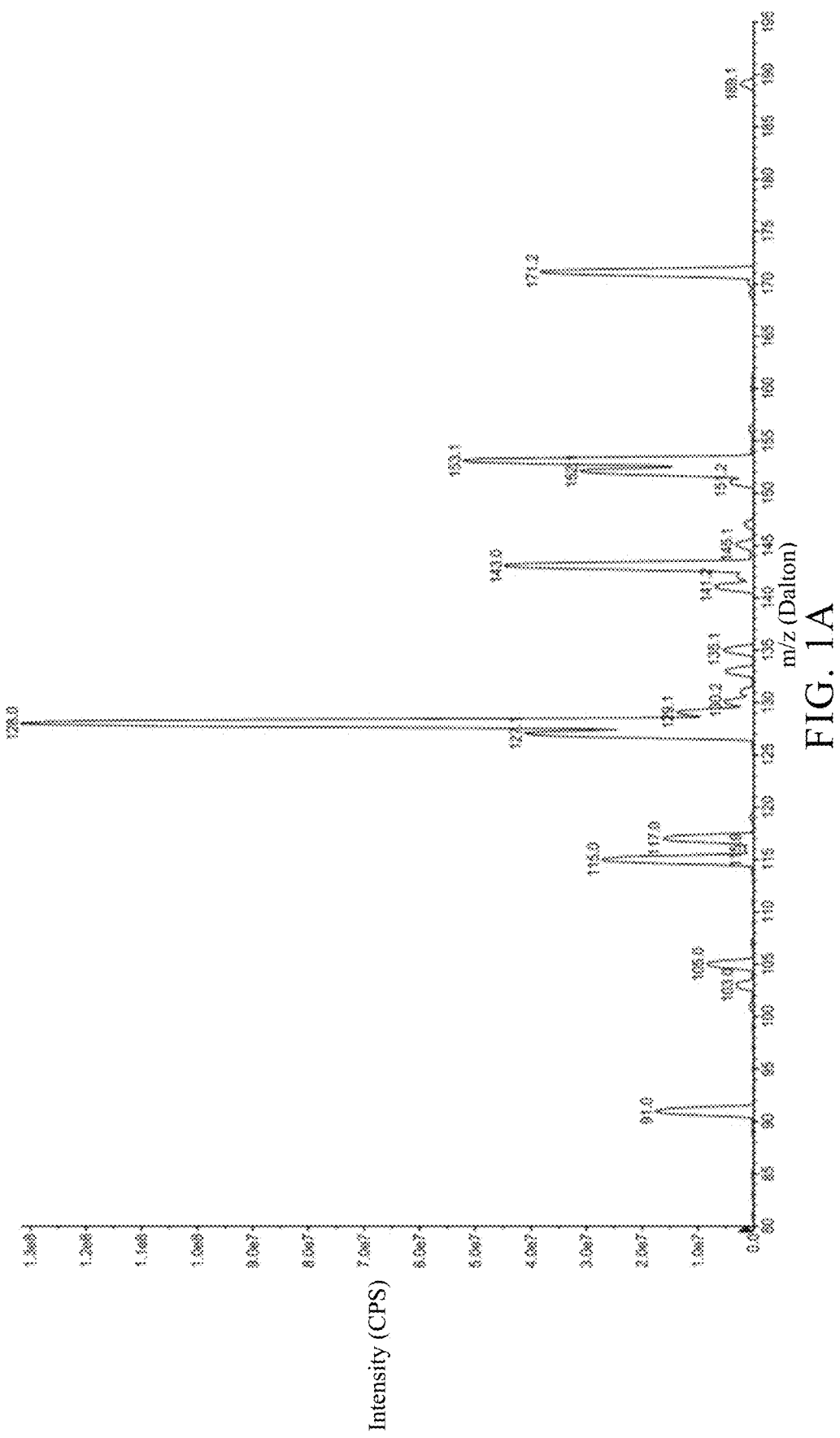

The following will describe some embodiments of the present invention in detail. However, without departing from the spirit of the present invention, the present invention may be embodied in various embodiments and should not be limited to the embodiments described in the specification. In addition, unless otherwise state herein, the expressions "a," "the," or the like recited in the specification of the present invention (especially in the claims) should include both the singular and the plural forms. Furthermore, the term "effective amount" used in this specification refers to the amount of the compound that can at least partially alleviate the condition that is being treated in a suspected subject when administered to the subject. The term "subject" used in this specification refers to a mammalian, including human and non-human animals. The term "mg/kg-body weight" used in this specification refers to the dosage (mg) required per kg-body weight. The term "hydrocarbyl" used in this specification refers to a saturated hydrocarbyl or an unsaturated hydrocarbyl with one or more π-bonds. The term "stem cell therapy" used in this specification refers to any treatment comprising administering to a subject a stem cell via any administration manner.

Telomere is a region of repetitive nucleotide sequences at each end of a chromatid. It has been known that the length of telomere may determine the longevity of a cell. Telomerase is a reverse transcriptase and can extend the length of telomeres, and thus plays an important role in regulating cell growth, maintaining cell homeostasis, and inhibiting cell apoptosis. As described above, previous researches reveal that a stem cell therapy does not have significant therapeutic effect on motor neuron degenerative diseases, which probably due to the short lifecycle of the transplanted stem cells. Therefore, if the lifecycle of the transplanted stem cells can be prolonged (e.g., the activity of telomerase can be enhanced), the therapeutic effect of stem cell therapy on motor neuron degenerative diseases could be improved.

Furthermore, it has been known that the brain-derived neurotrophic factor (BDNF), stromal cell-derived factor-1 (SDF1), and CXC chemokine receptor 4 (CXCR4) secreted from stem cells have an effect on inhibiting motor neuron apoptosis and promoting motor neuron proliferation, and thus, can be used to protect motor neurons (see "Park, D. et al., Human adipose tissue-derived mesenchymal stem cells improve cognitive function and physical activity in ageing mice. J Neurosci Res, 2013," which is entirely incorporated hereinto by reference). In another aspect, it has been known that the immune regulatory factors, such as interleukin 6 (IL-6), and interleukin 8 (IL-8), secreted from stem cells can maintain neurogenesis by regulating immune response (see Kohman, R. A. et al., "Neurogenesis, inflammation and behavior. Brain Behav Immun, 2013. 27 (1) : p. 22-32," which is entirely incorporated hereinto by reference). Accordingly, if the expression levels of BDNF, SDF1, CXCR4, and/or immune regulatory factors (e.g., IL-6, IL-8) of a stem cell can be increased, the therapeutic effect of stem cell therapy on motor neuron degenerative diseases can be improved.

The inventors of the present invention found that a phthalide can increase the expression levels of telomerase, brain-derived neurotrophic factor, stromal cell-derived factor-1, CXC chemokine receptor 4, and/or an immune regulatory factor (e.g., IL-6, and/or IL-8) of stem cells.

Accordingly, the present invention provides a method for providing an increased expression of at least one of telomerase, brain-derived neurotrophic factor, stromal cell-derived factor-1, CXC chemokine receptor 4, and an immune regulatory factor of a stem cell in a subject, comprising simultaneously or separately administering to the subject an effective amount of (a) a phthalide and (b) a stem cell, wherein said increased expression is increased in comparison with a corresponding expression of the effective amount of the stem cell in a subject that is not administered with the phthalide.

In one embodiment of the present invention, the phthalide suitable for the method of the present invention is selected from the group consisting of a compound of formula (I), a pharmaceutically acceptable salt of the compound of formula (I), a pharmaceutically acceptable ester of the com

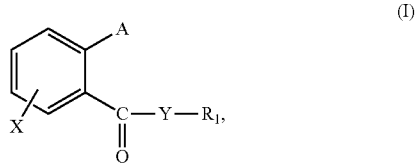

and combinations thereof:

wherein, A is a C1-C5 hydrocarbyl being optionally substituted by one or more substituents selected from the group consisting of —OH, =O, and C1-C3 hydrocarbyl; X

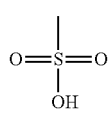

—Ol

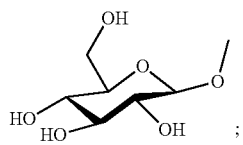

$R_1$ is H or a substituted or unsubstituted C1-C20 hydrocarbyl, wherein one or more —$CH_2$— in the hydrocarbyl are optionally replaced by —NH— or —O—; Y is O or S and optionally bonds with A to form a five-membered ring, with a proviso that when Y bonds with A to form a five-membered ring, $R_1$ is not present.

It is preferred that in the compound of formula (I), A is a C1-C5 alkyl or alkenyl being optionally substituted by one or more substituents selected from the group consisting of —OH, =O, and C1-C3 alkyl; and $R_1$, if present, is H or a substituted or unsubstituted C1-C10 hydrocarbyl, wherein one or more —$CH_2$— in the hydrocarbyl are optionally replaced by —NH— or —O—. Preferably, in the compound of formula (I), A is

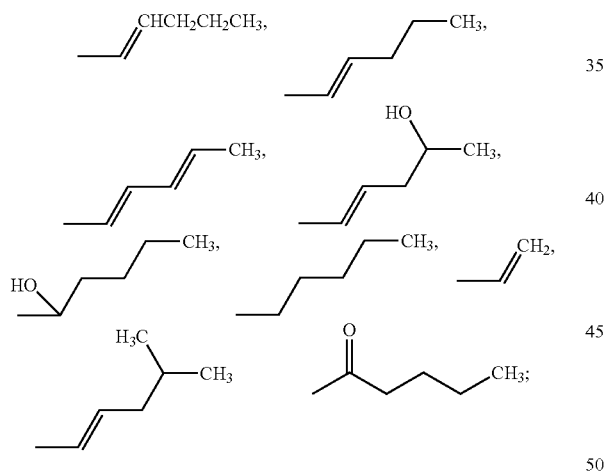

and $R_1$, if present, is H,

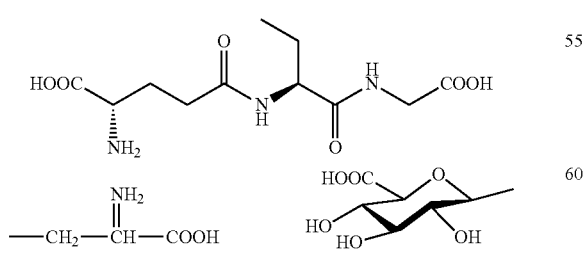

More preferably, the compound of formula (I) used as the phthalide in the method of the present invention is selected from the group consisting of the following compounds (1) to (14), a pharmaceutically acceptable salt thereof, a pharmaceutically acceptable ester thereof, and combinations thereof:

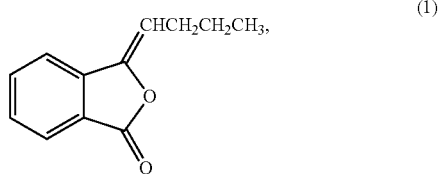
(1)

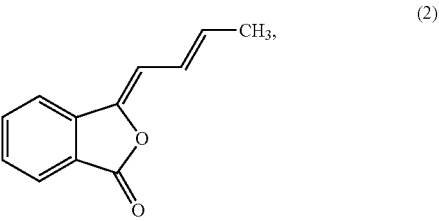
(2)

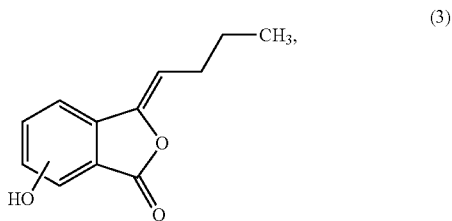
(3)

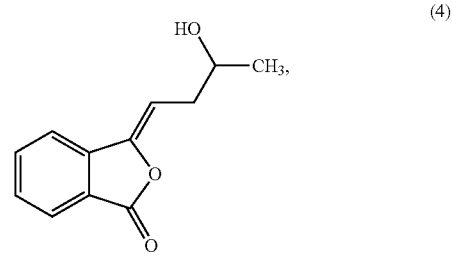
(4)

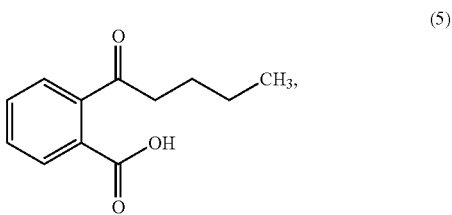
(5)

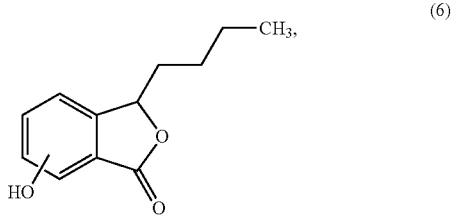
(6)

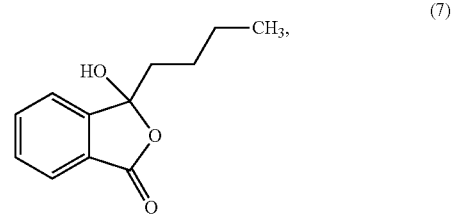
(7)

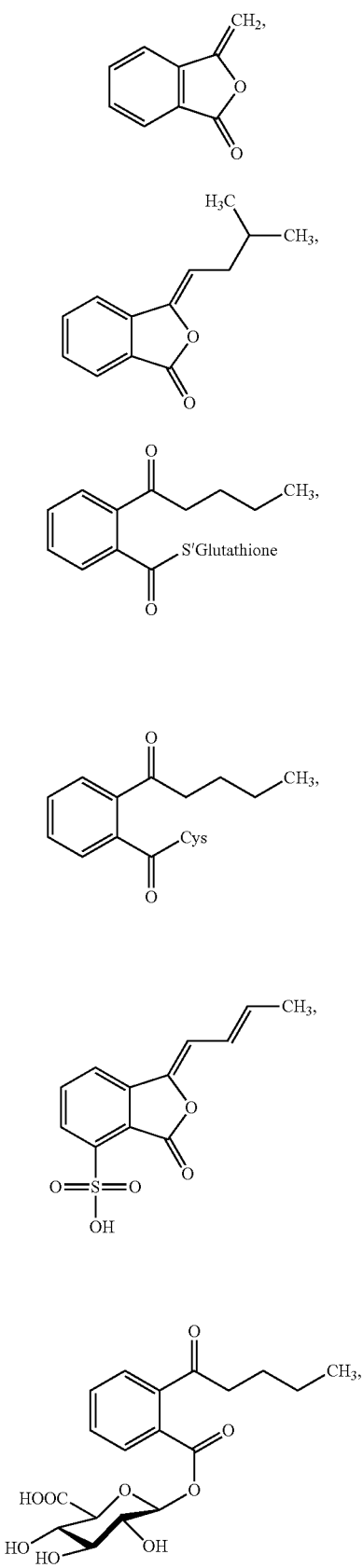
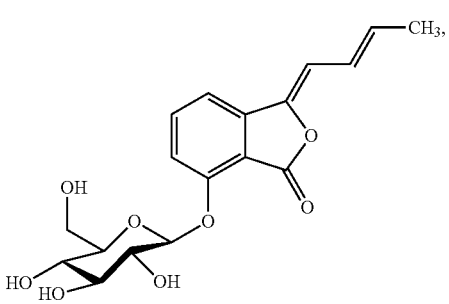

wherein the "Cys" in compound (10) refers to cysteine.

The inventors of the present invention found that a phthalide, when administered to an organism, can increase the expression levels of telomerase, brain-derived neurotrophic factor, stromal cell-derived factor-1, CXC chemokine receptor 4, and/or an immune regulatory factor of a stem cell. In the above compounds (1) to (14), the compound (1) is n-butylidenephthalide (BP), and the compounds (2) to (14) are metabolites of n-butylidenephthalide, namely, the compounds generated by the phase I or phase II metabolism of BP in an organism, which will be illustrated by the examples provided in this specification. It is believed that the pharmaceutical activity of a compound in an organism is provided from the metabolites of the compound. Therefore, the phthalide used in the method of the present invention is preferably any one of the compounds (1) to (14), a pharmaceutically acceptable salt thereof, a pharmaceutically acceptable ester thereof, or a combination thereof.

In addition to the compound of formula (I), the phthalide suitable for the method of the present invention may also be selected from other structural analogue of BP, a pharmaceutically acceptable salt thereof, a pharmaceutically acceptable ester thereof, and combinations thereof.

The term "pharmaceutically acceptable salt" used in this specification refers to a pharmaceutically acceptable salt prepared from said compound with acid functional groups and an organic or inorganic base. The salts formed with inorganic bases, include but not are limited to alkali metal salts (e.g., sodium salts, potassium salts), alkaline earth metal salts (e.g., calcium salts, magnesium salts), transition metal salts (e.g., iron salts, zinc salts, copper salts, manganese salts, and aluminum salts), and ammonium salts. The salts formed with organic bases, include but are not limited to the salts formed with methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like.

The term "pharmaceutically acceptable ester" used in this specification includes an ester prepared from the compound with —OH functional group and an acid. The acid may be an inorganic acid such as hydrochloric acid, hydrobromic acid, sulfuric acid, sulfamic acid, nitric acid, and phosphoric acid, or an organic acid such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, 2-hydroxy ethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, and undecanoic acid.

The term "structural analogue of BP" used in this specification refers to a compound which is not identical to BP, but is in part or whole similar to part or all of BP in terms of chemical structure, electron distribution or pharmaceutical characteristics. In addition to the compound of formula (I), examples of a structural analogue of BP include, but are not limited to, a metabolic precursor of BP, an isomer of BP or an isomer of a metabolic precursor of BP, and a pharmaceutically acceptable salt or ester thereof. The term "metabolic precursor of BP" used in this specification refers to a compound whose metabolism in an organism will generate BP. Specific examples of a structural analogue of BP include, but are not limited to, 3-butylidene-4,5-dihydrophthalide (ligustilide) and 3-butyl-3a,4,5,7a-tetrahydro-1(3H)-isobenzofuranone (cnidilide).

In some embodiments of the present invention, the phthalide used in the present invention is 3-butylidene-4,5-dihydrophthalide.

The stem cell used in the method of the present invention can be selected from any stem cells suitable for stem cell therapy, such as a stem cell selected from the group consisting of an embryonic stem cell, an adult stem cell (e.g., a mesenchymal stem cell, a hematopoietic stem cell), an induced pluripotent stem cell (iPSc), or a combination thereof. Examples of a mesenchymal stem cell include, but are not limited to a bone marrow stem cell, an umbilical cord blood stem cell, a placenta stem cell, an adipose stem cell (ADSC), an oral stem cell, an olfactory bulbs stem cell, amniotic fluid stem cell, amniotic stem cell, umbilical cord stem cell, and umbilical cord lining stem cell. In some embodiments of the method of the present invention, the stem cell is an adipose stem cell.

As described above, a combined use of a phthalide and a stem cell can increase the expression levels of telomerase, brain-derived neurotrophic factor, stromal cell-derived factor-1, CXC chemokine receptor 4, and an immune regulatory factor (e.g., interleukin-6 and interleukin-8) of the stem cell in a subject to inhibit the apoptosis of motor neurons, protect motor neurons, and improve the proliferation of motor neurons in the subject, and thus, it can be used for treating motor neuron degenerative diseases and/or delaying the onset of motor neuron degenerative diseases.

In some embodiments, the method of the present invention is to be used for treating motor neuron degenerative diseases and/or delaying the onset of motor neuron degenerative diseases. The motor neuron degenerative diseases comprise any diseases related to the degeneration of motor neurons, including but not limited to amyotrophic lateral sclerosis (ALS), myasthenia gravis, gravis, muscular atrophy, muscular dystrophy, multiple sclerosis, multiple system atrophy, and spinal muscular atrophy.

According to an embodiment of the method of the present invention, the method is used for treating amyotrophic lateral sclerosis. It is known that patients with amyotrophic lateral sclerosis will gradually show muscular atrophy, which usually causes quadriplegia, difficulty swallowing and even respiratory failure in 2 to 5 years. Researches have shown that amyotrophic lateral sclerosis may be related to excessive neuronal excitation (e.g., excessive accumulation of glutamates). Therefore, at present, the glutamate antagonist, such as Riluzole, is primarily used in clinic to treat motor neurodegenerative diseases to increase the survival rate of the patients. As compared with the administration of Riluzole, the method of the present invention can more effectively delay the onset of motor neuron degenerative diseases and increase the survival rate of the patients.

In the method of the present invention, the phthalide and the stem cell can independently be administered as a separate pharmaceutical composition. The pharmaceutical composition comprising a phthalide and the pharmaceutical composition comprising a stem cell can be simultaneously or separately administered into a patient in need of such treatment.

The pharmaceutical composition comprising a phthalide and the pharmaceutical composition comprising a stem cell both can be manufactured into a medicament of any suitable form for administration. For example, the pharmaceutical composition comprising a phthalide can be manufactured into a medicament in a form suitable for oral administration, nasal administration, corticospinal tract injection, intrathecal injection, intracerebral injection, intravenous injection, intraperitoneal injection, and/or subcutaneous injection, but is not limited thereby. The pharmaceutical composition comprising a stem cell can be manufactured into a medicament with a form suitable for corticospinal tract injection, intrathecal injection, intracerebral injection, intravenous injection, intraperitoneal injection, and/or subcutaneous injection. According to some embodiments of the method of the present invention, the phthalide is administered as a pharmaceutical composition in a form suitable for oral administration, such as in a form of a tablet, a capsule, a granule, powder, a fluid extract, a solution, syrup, a suspension, an emulsion or a tincture, and the stem cell is administered as a pharmaceutical composition in a form suitable for intracerebral injection or intravenous injection. Depending on the form and purpose of the medicament, the pharmaceutical composition comprising a phthalide and the pharmaceutical composition comprising a stem cell may further comprise a pharmaceutically acceptable carrier.

For a formulation suitable for oral administration, the pharmaceutical composition can comprise a pharmaceutically acceptable carrier which has no adverse influence on the activity of the active component (i.e., the phthalide) comprised therein, such as a solvent, oily solvent, diluent, stabilizer, absorption delaying agent, disintegrant, emulsifier, antioxidant, binder, lubricants, and moisture absorbent. The pharmaceutical composition can be prepared as a medicament for oral administration by any suitable method.

As for a formulation suitable for corticospinal tract injection, intrathecal injection, intracerebral injection, intravenous injection, or subcutaneous injection, the pharmaceutical composition may comprise one or more components, such as an isotonic solution, a saline buffer solution (e.g., a phosphate buffer solution or a citrate buffer solution), a solubilizer, an emulsifier, and other carriers to manufacture the medicament as an intravenous injection, an emulsion intravenous injection, a powder injection, a suspension injection, or a powder-suspension injection.

In addition to the above adjuvants, each of the pharmaceutical composition comprising a phthalide and the pharmaceutical composition comprising a stem cell may optionally comprise other addatives, such as a flavoring agent, a toner, a coloring agent, etc. to enhance the taste and visual appeal of the resultant medicament. To improve the storability of the resultant formulation, the pharmaceutical composition may also comprise a suitable amount of a preservative, a conservative, an antiseptic, an anti-fungus reagent, etc. Furthermore, the pharmaceutical composition may comprise one or more other active components, such as an antioxidant (e.g., vitamin E), neurotrophic factor, immune modulator, etc., to further enhance the efficacy of the method of the present invention or increase the application flexibility and adaptability for the composition, as long as the other active components have no adverse effect on the phthalide and the stem cell in the method of the present invention.

In the method of the present invention, the pharmaceutical composition comprising a phthalide and the pharmaceutical composition comprising a stem cell can be simultaneously or separately administered to a subject in need of such treatment. Namely, the pharmaceutical composition comprising a phthalide can be administered into a subject before, after, or simultaneously with the administration of the pharmaceutical composition comprising a stem cell. Furthermore, each of the pharmaceutical composition comprising a phthalide and the pharmaceutical composition comprising a stem cell can be applied with various administration frequencies, such as once a day, several times a day or once for days, etc.

Depending on the requirements of the subject, the dosage of the phthalide and the stem cell of the present invention can be adjusted. For example, when applied to the human body for treating motor neuron degenerative diseases and/or delaying the onset of motor neuron degenerative diseases, the phthalide is preferably administered at an amount ranging from about 100 mg/kg-body weight to about 1,000 mg/kg-body weight per day, more preferably about 250 mg/kg-body weight to about 800 mg/kg-body weight per day. The stem cell is preferably administered at an amount ranging from about $1\times10^2$ cells/site to about $1\times10^{15}$ cells/site and more preferably about $1\times10^5$ cells/site to about $1\times10^8$ cells/site. However, for patients with acute conditions, the dosage can be increased to several times or several tens of times, depending on the practical requirements. In one embodiment of the method of the present invention for treating amyotrophic lateral sclerosis, the phthalide is BP and its dosage is about 500 mg/kg-body weight per day, and the stem cell is adipose stem cells and its dosage is about $2\times10^6$ cells via intracerebral injection along with $1\times10^6$ cells via intravenous injection.

The present invention also provides a kit. The kit comprises a first composition comprising a phthalide and a second composition comprising a stem cell, wherein the first composition and the second composition are to be administered to a subject in need simultaneously or separately. In addition, when use the kit of the present invention, the first composition and the second composition can be applied with various administration frequencies, such as once a day, several times a day or once for days, etc. The properties and features of the phthalide and the stem cell and the preferably embodiments thereof are all as described hereinabove.

The kit of the present invention can be used for providing an increased expression of at least one of telomerase, brain-derived neurotrophic factor, stromal cell-derived factor-1, CXC chemokine receptor 4, and an immune regulatory factor (e.g., interleukin-6 and interleukin-8) of a stem cell in a subject. Therefore, the kit of the present invention can be used for inhibiting the apoptosis of motor neurons, protecting motor neurons, and/or improving the proliferation of motor neurons in the subject, and thus, it can be used for treating motor neuron degenerative diseases and/or delaying the onset of motor neuron degenerative diseases. Preferably, the kit of the present invention is used for treating spinal motor neuron degenerative diseases and/or delaying the onset of spinal motor neuron degenerative diseases. The motor neuron degenerative diseases comprise any diseases related to the degeneration of motor neurons, including but not limited to amyotrophic lateral sclerosis, myasthenia gravis, gravis, muscular atrophy, muscular dystrophy, multiple sclerosis, multiple system atrophy, spinal muscular atrophy, etc. According to an embodiment of the present invention, the kit is used for treating amyotrophic lateral sclerosis.

In the kit of the present invention, the first composition and the second composition are preferably placed in different packages, such as different plastic bags, plastic bottles, glass bottles, ampoules, cartons or plastic boxes. The packages can be connected to or separated from each other. In addition, the first composition and the second composition can independently be in the same or different form for administration. For example, the first composition and the second composition can independently be administered to a subject in need of such treatment via oral administration, nasal administration, corticospinal tract injection, intrathecal injection, intracerebral injection, intravenous injection, intraperitoneal injection, and/or subcutaneous injection but is not limited thereby. According to some embodiments of the present invention, the first composition is in a form for oral administration (e.g., a tablet), and the second composition is placed in a glass bottle and in a form suitable for intracerebral injection or intravenous injection.

Depending on the form and purpose, the first composition and the second composition may further comprise any pharmaceutically acceptable carriers, adjuvants, and additives to be prepared in a desired form for administration, as long as the carriers, adjuvants, and additives have no adverse effect on the phthalide and the stem cell in the kit of the present invention.

For a formulation suitable for oral administration, each of the first composition and the second composition can independently comprise a pharmaceutically acceptable carrier which has no adverse influence on the activity of the active component (i.e., the phthalide or the stem cell) comprised therein, such as a solvent, oily solvent, diluent, stabilizer, absorption delaying agent, disintegrant, emulsifier, antioxidant, binder, lubricants, and moisture absorbent. The first composition and/or the second composition can be prepared as a formulation for the oral administration by any suitable method, such as a tablet, a capsule, a granule, powder, a fluid extract, a solution, syrup, a suspension, an emulsion, a tinctures, etc.

As for a formulation suitable for corticospinal tract injection, intrathecal injection, intracerebral injection, intravenous injection, or subcutaneous injection, the first composition and the second composition may independently comprise one or more components, such as an isotonic solution, a saline buffer solution (e.g., a phosphate buffer solution or a citrate buffer solution), a solubilizer, an emulsifier, and other carriers to provide a formulation of intravenous injection, an emulsion intravenous injection, a powder injection, a suspension injection, a powder-suspension injection, etc.

In addition to the above adjuvants, the first composition and/or the second composition may optionally comprise other additives, such as a flavoring agent, a toner, a coloring agent, etc. to enhance the taste and visual appeal of the resultant formulation. To improve the storability of the resultant formulation, the first composition and/or the second composition may also comprise a suitable amount of a preservative, a conservative, an antiseptic, an anti-fungus reagent, etc.

Furthermore, the first composition and/or the second composition in the kit of the present invention may optionally comprise one or more other active components to further enhance the efficacy of the method of the present invention or increase the application flexibility and adaptability of the resultant formulation, as long as the other active components have no adverse effect on the phthalide and the stem cell of the present invention.

In addition, depending on the practical requirements, the amount of the first composition and the second composition in the kit of the present invention can be adjusted to that suitable for single or multiple use. Therefore, the kit of the present invention may optionally further comprise an instruction showing the manner for using the first composition and the second composition.

For example, when applied to the human body for treating motor neuron degenerative diseases and/or delaying the onset of motor neuron degenerative diseases, the dosage of the first composition, based on the amount of the phthalide, is preferably from about 100 mg/kg-body weight to about 1,000 mg/kg-body weight per day, and more preferably from about 250 mg/kg-body weight to about 800 mg/kg-body weight per day. The dosage of the second composition, based on the amount of the stem cells, is preferably from about $1 \times 10^2$ cells/site to about $1 \times 10^{15}$ cells/site, and more preferably from about $1 \times 10^5$ cells/site to about $1 \times 10^8$ cells/site. However, for patients with acute conditions, the dosage can be increased to several times or several tens of times, depending on the practical requirements. In one embodiment using the kit of the present invention to treat amyotrophic lateral sclerosis, the phthalide is BP and its dosage is about 500 mg/kg-body weight per day, and the stem cell is adipose stem cell and its dosage is about $2 \times 10^6$ cells/site via intracerebral injection and $1 \times 10^6$ cells/site via intravenous injection.

The kit of the present invention may further comprise a third composition which comprises a solvent or a solution. The third composition is preferably placed in a package different from that of the first composition and the second composition (e.g., a plastic bag, a plastic bottle, a glass bottle or an ampoule), and can be mixed with the first composition and/or the second composition to provide a solution for injection. The solvents suitable for the third composition includes, but is not limited to a polar solvent, such as water, DMSO and ethanol. The solution suitable for the third composition includes, but is not limited to saline buffer solutions and any other injection solutions suitable for providing an injection formulation. Examples of the saline buffer solution include, but are not limited to a phosphate buffer solution (PBS), a citrate buffer solution, and a physiological saline, etc. In one embodiment, the second composition is mixed with the third composition before being administered to a subject to provide a formulation suitable for injection.

In addition, the inventors of the present invention found that a metabolic precursor of a phthalide also has the effects of treating a motor neuron degenerative disease and/or delaying the onset of a motor neuron degenerative disease, and the efficacy of the metabolic precursor of a phthalide is not only superior than using BP alone, but also superior than using a combination of BP and a stem cell. Therefore, the present invention also provide a method for treating a motor neuron degenerative disease and/or delaying the onset of a motor neuron degenerative disease in a subject, comprising administering to the subject an effective amount of a metabolic precursor of a phthalide, wherein the metabolic precursor of a phthalide is 3-butylidene-4,5-dihydrophthalide (ligustilide).

According to the present invention, a metabolic precursor of a phthalide can be used for treating and/or delaying the onset of at least one of amyotrophic lateral sclerosis, myasthenia gravis, myasthenia, muscular atrophy, muscular dystrophy, multiple sclerosis, multiple system atrophy, and spinal muscular atrophy, and especially can be used for treating and/or delaying the onset of amyotrophic lateral sclerosis. The formulation, administration, and dosage of the precursor are all as described hereinabove.

The present invention will be further illustrated in details with specific examples as follows. However, the following examples are provided only for illustrating the present invention, and the scope of the present invention is not limited thereby.

EXAMPLES

Example 1

Identification of the Metabolites of Butylidenephthalide

It has been known that the medicine metabolic pathway within an organism's liver can be primarily divided into phase I and phase II metabolism. Phase I metabolism occurs mainly by the redox reaction or hydrolysis reaction of medicine, while phase II metabolism occurs mainly by cytochrome P450 (CYP450) monoxygenase system. This example simulated the phase I and II metabolism of butylidenephthalide that occur within an organism's liver by respectively mixing butylidenephthalide with hepatic microsomes or cryopreserved hepatocytes in vitro. The products in the reaction solution were analyzed by liquid chromatograph-tandem mass spectrometer (LC-MS/MS) to identify the metabolites and the metabolic profile. The experimental steps were as follows:

(1) Phase I Metabolism Assay n-Butylidenephthalide (comprising Z-BP 95%+E-BP 5%; purchased from ECHO Chemical) (2 mM) was mixed respectively with $K_3PO_4$ buffer solution (100 mM, pH7.4) containing human, rats or dogs hepatic micrsomes (0.5 mg/mL). The mixture was maintained at 37° C. for 10 minutes, and then pre-warmed cofactors (NADPH (2 mM) and $MgCl_2$ (3 mM)) were added thereto and the mixture was incubated at 37° C. for 60 minutes. Thereafter, 3-fold volume of acetonitrile containing 0.1% formic acid was added to the mixture to terminate the reaction. The mixture was centrifuged at 13000 rpm for 5 minutes. The supernatant was then collected and analyzed by LC-MS/MS to identify the metabolites.

(2) Phase II Metabolism Assay

William's E medium containing $5 \times 10^5$ thawed human, rat or dog hepatocytes were respectively added into a 12-well culture dish, and the cells were cultured for 6 hours. Then, 0.5 mL of n-butylidenephthalide (comprising Z-BP 95%+ E-BP 5%; purchased from ECHO Chemical) (50 μM) was added into the culture dish. After the cells were incubated at 37° C., 95% relative humidity and 5% $CO_2$ for 6 hours, 2 mL of acetonitrile (100%) was added to terminate the reaction. The sample was collected, mixed adequately, and centrifuged at 45000 g, 4° C. for 10 minutes. The supernatant was then collected, dried, and analyzed by LC-MS/MS to identify the metabolites of n-butylidenephthalide.

(3) LC-MS/MS Analysis

The samples obtained from (1) and (2) were separately dissolved in acetonitrile/0.1% formic acid, centrifuged at 45000 g, 4° C. for 10 minutes. Then, an aliquot (20 μl) of each sample was injected into an autosampler vial (Agilent Technologies, USA) of a LC-MS/MS system to perform LC-MS/MS analysis. The LC-MS/MS system comprises an ABSCIEX 5500 Q TRAP™ system with 1200SL HPLC system (Agilent Technologies, USA), a HPLC column (Symmetry® C18, 3.5 μM, 4.6×75 mm), and a autosampler (Agilent Technologies, USA). A two-solvent system (solvent A: 0.1% formic acid; solvent B: methanol containing 0.1% formic acid) was used to perform HPLC at a flow rate of 0.8 mL/min. The HPLC gradient system was set as follows: 0 to 2 minutes held at 10% solvent B; 2 to 7 minutes with a gradient from 10% to 95% solvent B; 7 to 12 minutes held at 95% solvent B; 12 to 14 minutes with a gradient from 95% to 10% solvent B; 14 to 20 minutes held at 10% solvent B; and the retention time of HPLC analysis is 20 minutes. The mass spectrometry analysis was performed in positive ion electrospray ionization (+ESI) mode at 5.5 kV, 550° C., and $N_2$ (nitrogen) was used as an auxiliary gas. The most intense peaks in the LC-MS/MS spectrum and the mass-shifted peaks in the LC-MS/MS spectrum of each sample as compared to n-butylidenephthalide spectrum were analyzed by LightSight™ Software to determine the metabolites in the samples and identifying the biotransformation pathway and metabolic profile of n-butylidenephthalide in an organism. The results are shown in Table 1, Table 2, FIG. 1A, FIG. 1B and FIG. 1C.

FIG. 1A shows the fragment product spectrum of the mixture of n-butylidenephthalide (m/z 189.1) and human hepatic microsomes analyzed by LC-MS/MS. As shown in FIG. 1A, the most intense peaks (m/z) are 171.2 amu, 153.1 amu, 143.0 amu, 128.0, and 115.0 amu.

Figure 1B:
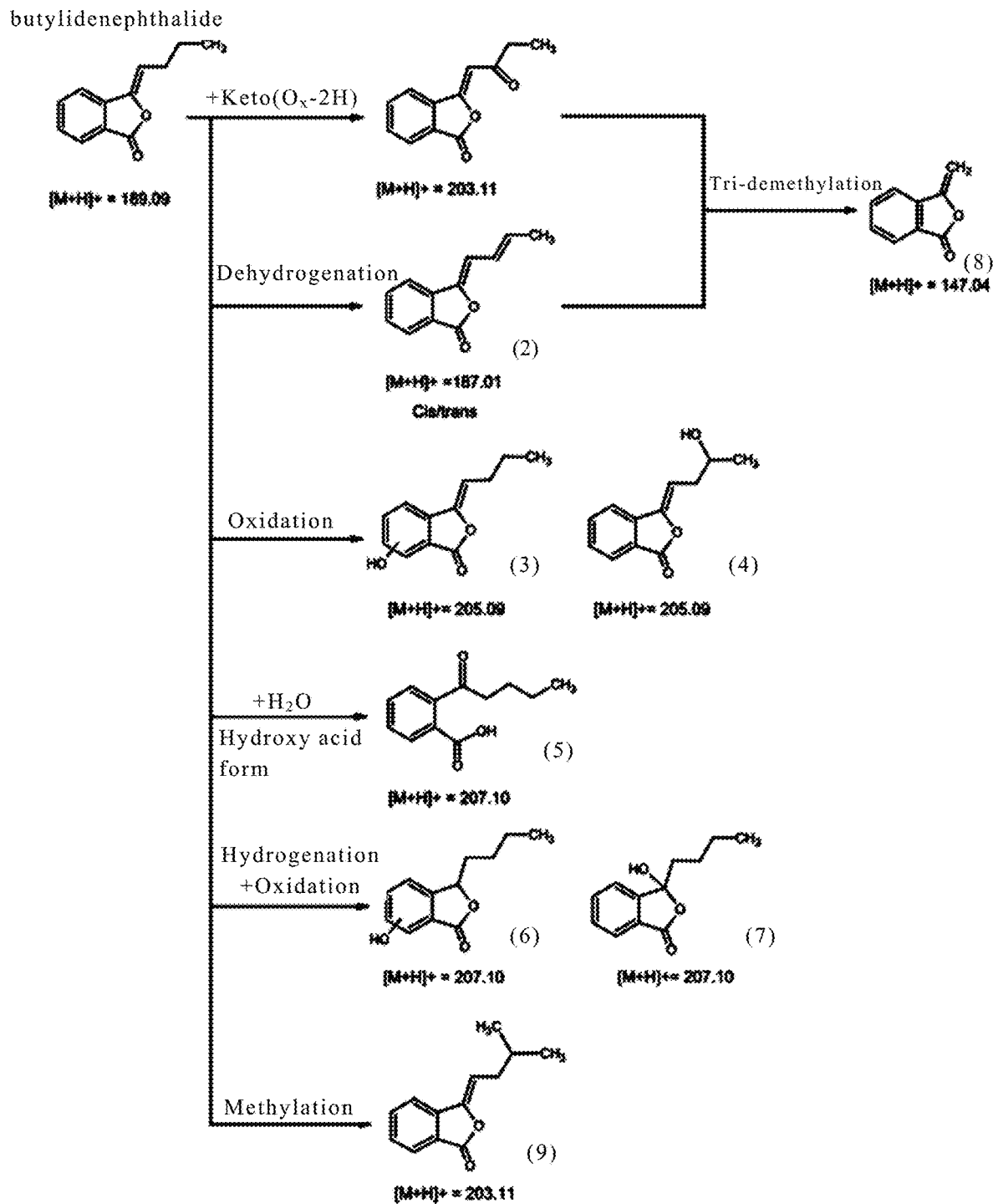

Table 1 shows the types of metabolites produced from the reaction of the mixture of n-butylidenephthalide and hepatic microsomes (i.e., phase I metabolism) and the biotransformation pathway acquired by software analysis. The results show that the compounds (2) to (9) of the present invention can be produced by the reaction of a mixture of n-butylidenephthalide and the hepatic microsomes of rat, dog or human, indicating that n-butylidenephthalide can be transformed to similar metabolites when metabolized in the livers of different organisms. FIG. 1B shows the metabolic profile obtained from the reaction of the mixture of n-butylidenephthalide and hepatic microsomes, and the chemical structures of compounds (2) to (9).

TABLE 1

Phase I metabolites

| Species | Metabolites | Biotransformation pathway | Mass-shifted peaks |
|---|---|---|---|
| Rat | Compound (2) | Dehydrogenation | m/z 189→187 |
|  | Compound (3); Compound (4) | Oxidation | m/z 189→205 |
|  | Compound (5); Compound (6); Compound (7) | Hydrogenation (forming hydrocarbyl group) | m/z 189→207 |
|  | Compound (8) | Tri-Demethylation | m/z 189→147 |
|  | Compound (9) | +Keto ($O_x$—2H) or methylation | m/z 189→203 |

TABLE 1-continued

Phase I metabolites

| Species | Metabolites | Biotransformation pathway | Mass-shifted peaks |
|---|---|---|---|
| Dog | Compound (2) | Dehydrogenation | m/z 189→187 |
|  | Compound (3); Compound (4) | Oxidation | m/z 189→205 |
|  | Compound (5); Compound (6); Compound (7) | Hydrogenation (forming hydrocarbyl group) | m/z 189→207 |
|  | Compound (8) | Tri-Demethylation | m/z 189→147 |
|  | Compound (9) | +Keto ($O_x$—2H) or methylation | m/z 189→203 |
| Human | Compound (2) | Dehydrogenation | m/z 189→187 |
|  | Compound (3); Compound (4) | Oxidation | m/z 189→205 |
|  | Compound (5); Compound (6); Compound (7) | Hydrogenation (forming hydrocarbyl group) | m/z 189→207 |
|  | Compound (8) | Tri-Demethylation | m/z 189→147 |
|  | Compound (9) | +Keto ($O_x$—2H) or methylation | m/z 189→203 |

Figure 1C:
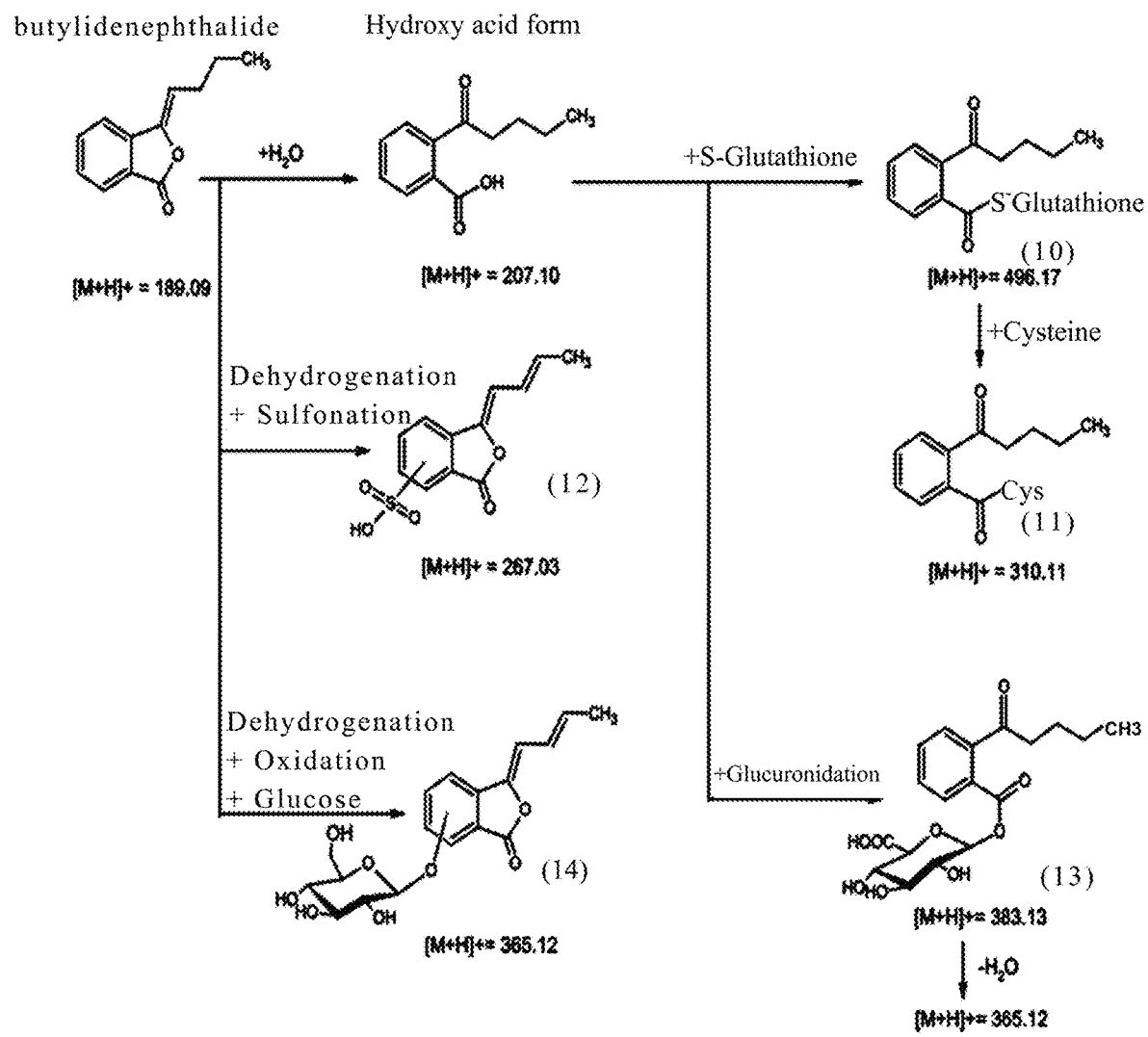

Table 2 shows the types of metabolites produced from the reaction of the mixture of n-butylidenephthalide and cryopreserved hepatocytes (i.e., phase II metabolism) and the biotransformation pathway acquired by software analysis. The results show that compounds (11) to (14) of the present invention can be produced by the reaction of a mixture of n-butylidenephthalide and the cryopreserved hepatocytes of rat, dog or human, indicating that butylidenephthalide can be transformed to similar metabolites when metabolized in the livers of different organisms. FIG. 1C shows the metabolic profile obtained from the reaction of the mixture of n-butylidenephthalide and cryopreserved hepatocytes, and the chemical structures of compounds (11) to (14).

TABLE 2

Phase II metabolites

| Species | Metabolites | Biotransformation pathway | Mass shift |
|---|---|---|---|
| Rat | Compound (11) | + Cysteine | m/z 189→310 |
|  | Compound (10) | +S-Glutathione | m/z 189→496 |
|  | Compound (12) | Dehydrogenation + Sulfonation | m/z 189→267 |
|  | Compound (13) | Glucoronidation | m/z 189→365 |
| Dog | Compound (11) | +Cysteine | m/z 189→310 |
|  | Compound (10) | +S-Glutathione | m/z 189→496 |
|  | Compound (13) | Glucoronidation | m/z 189→365 |
|  | Compound (14) | Dehydrogenation + Oxidation + Glucose | m/z 189→365 |
| Human | Compound (11) | +Cysteine | m/z 189→310 |
|  | Compound (10) | +S-Glutathione | m/z 189→496 |
|  | Compound (12) | Dehydrogenation + Sulfonation | m/z 189→267 |
|  | Compound (13) | +Glucoronidation | m/z 189→365 |

Example 2

In Vivo Analysis: the Combination of Butylidenephthalide and ADSCs Increases the Survival Rate of Transgenic Mice It has been known that about 20% of amyotrophic lateral sclerosis patients were associated with mutations in the gene that encodes Cu/Zn superoxide dismutase enzyme (SOD1), and G93A was the major mutation site. The mice transfected with human mutant SOD1-G93A by gene transfection technique (hereafter referred to as SOD1-G93A transgenic mice)

was used as an animal model for the clinical study of amyotrophic lateral sclerosis since the mice exhibit a similar course of disease to human. A SOD1-G93A transgenic mouse will show the symptoms of amyotrophic lateral sclerosis within about 90±5 days postnatal and will die within about 125±5 days postnatal.

This example used the above SOD1-G93A transgenic mice as the object of study to perform in vivo analysis. The mice were randomly distributed into following six groups at 60-day-old: (A) control group (untreated); (B) Riluzole-treated group: the mice were treated with Riluzole at a dosage of 16 mg/kg-body weight once daily via intraperitoneal injection; (C) BP-treated group (BP 500 mg/kg/qd): the mice were treated with BP (comprising Z-BP 95%+E-BP 5%; purchased from ECHO Chemical) at a dosage of 500 mg/kg-body weight once daily via oral administration; (D) BP-treated group (BP 250 mg/kg/bid): the mice were treated with BP (comprising Z-BP 95%+E-BP 5%; purchased from ECHO Chemical) at a dosage of 250 mg/kg-body weight twice daily via oral administration; (E) combined treated group (combine BP with adipose tissue stem cells (ADSCs)): the mice were treated with BP (comprising Z-BP 95%+E-BP 5%; purchased from ECHO Chemical) at a dosage of 500 mg/kg-body weight once daily via oral administration, transplanted with ADSCs ($2\times10^6$ cells/30 μl PBS) via intracerebral injection once at 60 days postnatal, and then again transplanted with ADSCs ($1\times10^6$ cells/150 μl PBS) via intravenous injection at 90 days postnatal; (F) ligustilide-treated group: the mice were treated with ligustilide (3-butylidene-4,5-dihydrophthalide; purchased from Pharmaron) at a dosage of 500 mg/kg-body weight once daily via oral administration. After the SOD1-G93A transgenic mice were treated for 30 days, they were observed to see if a combined use of BP and ADSCs can prolong the longevity of the SOD1-G93A transgenic mice (i.e., more than 125 days). The results are shown in FIG. 2 and Table 3.

TABLE 3

| Group | Survival days |
| --- | --- |
| control group (n = 14) | 126.4 ± 7.2 |
| Riluzole-treated group (n = 3) | 133.7 ± 6.4 |
| BP-treated group (BP 500 mg/kg/qd) (n = 8) | 149.1 ± 4.4 |
| BP-treated group (n-BP 250 mg/kg/bid) (n = 3) | 217.7 ± 23.2 |
| combined treated group (ADSC + BP) (n = 4) | 185 ± 7.5 |
| ligustilide-treated group (n = 5) | 201.2 ± 6.0 |

Figure 2:
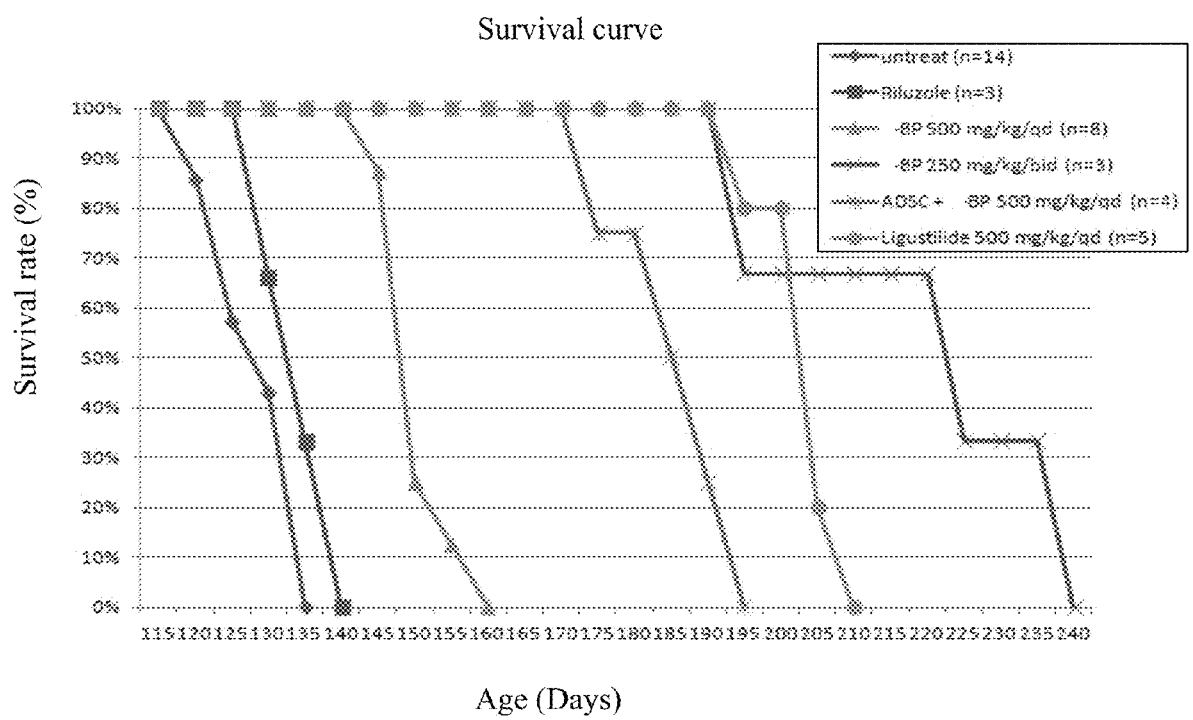
FIG. 2 shows the survival curves of various treatments on SOD1-G93A transgenic mice.

As shown in FIG. 2 and Table 3, the longevity of the mice in Riluzole-treated group (survived for about 133.7±6.4) was merely prolonged for about 7.3±0.8 days as compared to the untreated SOD1-G93A transgenic mice in the control group (survived for about 126.4±7.2). The longevity of the mice in BP-treated group (BP 500 mg/kg/qd) (survived for about 149.1±4.4) was prolonged for about 22.7±2.8 days; the longevity of the mice in BP-treated group (n-BP 250 mg/kg/bid) (survived for about 217.7±23.2) was prolonged for about 91.3±16 days. The longevity of the mice in combined treated group (survived for about 185±7.5) was prolonged for about 58.6±0.3 days; and the longevity of the mice in ligustilide-treated group (survived for about 201.2±6.0) was prolonged for about 74.8±1.2 days.

The above results show that as compared with the use of Riluzole or BP once daily alone, the present invention combining BP and ADSCs can more effectively increase the survival rate of the mice suffering from amyotrophic lateral sclerosis. In addition, the use of ligustilide (i.e., a metabolic precursor of a phthalide) or BP twice daily alone can effectively increase the survival rate of the mice suffering from amyotrophic lateral sclerosis, and the increased survival rate is not only much higher than the use of BP once daily alone, but also higher than the use of a combination of BP and ADSCs.

Example 3

In Vivo Analysis: the Combination of BP and ADSCs Delays the Onset of Amyotrophic Lateral Sclerosis This example used the above SOD1-G93A transgenic mice as the object of study to perform in vivo analysis. The mice were randomly distributed into following six groups at 60-days old: (A) control group (untreated); (B) Riluzole-treated group: the mice were treated with Riluzole at a dosage of 16 mg/kg-body weight once daily via intraperitoneal injection; (C) BP-treated group (BP 500 mg/kg/qd): the mice were treated with BP (comprising Z-BP 95%+E-BP 5%; purchased from ECHO Chemical) at a dosage of 500 mg/kg-body weight once daily via oral administration; (D) BP-treated group (BP 250 mg/kg/bid): the mice were treated with BP (comprising Z-BP 95%+E-BP 5%; purchased from ECHO Chemical) at a dosage of 250 mg/kg-body weight twice daily via oral administration; (E) combined treated group (combine BP with adipose tissue stem cells (ADSCs)): the mice were treated with BP (comprising Z-BP 95%+E-BP 5%; purchased from ECHO Chemical) at a dosage of 500 mg/kg-body weight once daily via oral administration, transplanted with ADSCs ($2\times10^6$ cells/30 μl PBS) via intracerebral injection once at 60 days postnatal, and then again transplanted with ADSCs ($1\times10^6$ cells/150 μl PBS) via intravenous injection at 90 days postnatal; (F) ligustilide-treated group: the mice were treated with ligustilide (3-butylidene-4,5-dihydrophthalide; purchased from Pharmaron) at a dosage of 500 mg/kg-body weight once daily via oral administration.

After the mice were treated for 30 days, the hind limbs of the mice were examined by BBB scale (Basso, Beattie, and Bresnahan (BBB) Locomotor Rating Scale). The BBB scale of the hind limbs of normal mice was 21 points, while the BBB scale of disease-progressed SOD1-G93A transgenic mice decreased from 21 to 0 points, wherein the lower scale represents a more severe action disorder in the mice. BBB scale is used to record the efficiency of the treatments.

Figure 3:
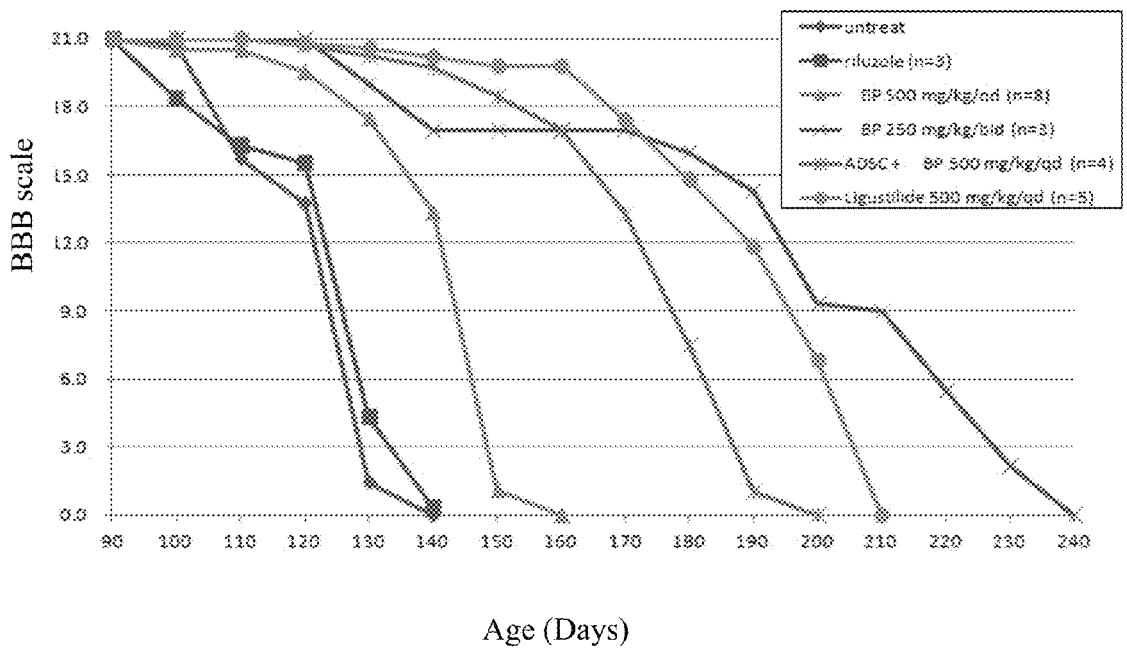
FIG. 3 shows the BBB-scaled curves of various treatments on SOD1-G93A transgenic mice.

As shown in FIG. 3, the BBB scale of the hind limbs of the untreated mice in the control group decreased rapidly after 110 days (from 19 to 0 points). The BBB scale of the hind limbs of the mice in the Riluzole-treated group decreased slowly from 90 to 125 days (from 21 to 16 points), and decreased rapidly after 125 days (from 16 to 0 points). The BBB scale of the hind limbs of the mice in the BP-treated group (BP 500 mg/kg/qd) decreased slowly from 125 to 135 days (from 21 to 16 points), and decreased rapidly after 135 days (from 16 to 0 points). The BBB scale of the hind limbs of the mice in the ligustilide-treated group decreased slowly from 130 to 170 days (from 21 to 18 points), and decreased rapidly after 170 days (from 18 to 0 points). The BBB scale of the hind limbs of the mice in the combined treated group decreased slowly from 150 to 190 days (from 21 to 0 points). The above results show that a combined use of BP and ADSCs indeed can delay the onset of amyotrophic lateral sclerosis. In addition, as compared with the use of Riluzole or BP alone, the present invention combining BP and ADSCs can more effectively delay the onset of amyotrophic lateral sclerosis.

The above results show that as compared with the use of Riluzole or BP once daily alone, the present invention combining BP and ADSCs can more effectively delay the onset of amyotrophic lateral sclerosis. In addition, the use of ligustilide can effectively increase the survival rate of the mice suffering from amyotrophic lateral sclerosis. The increased survival rate is not only much higher than the use of BP once daily alone, but also higher than the use of a combination of BP and ADSCs.

Example 4

In Vitro Study: Increase the Telomerase Expression Level of ADSCs after BP Treatment Human ADSCs were isolated from human adipose tissue by the following steps. Human adipose tissue from clinical research was washed with equal volumes of phosphate-buffered saline (PBS) and minced with fine scissors. Then, the tissue was digested with 0.075% collagenase type I (Sigma-Aldrich Co., St. Louis, Mo., USA) at 37° C. for 30 to 60 minutes, and a Dulbecco's modified Eagle's medium (DMEM)/F-12 (Invitrogen, Carlsbad, Calif., USA) containing 10% fetal bovine serum (FBS, Invitrogen) was added to terminate the digestion. The digested adipose tissue cells were filtered through a 100 μm nylon mesh to remove the cellular debris. The cell suspension was centrifuged for 10 minutes to obtain a pellet and cultured at 37° C., 5% $CO_2$ in a culture media (DMEM/F-12 containing 10% FBS, 100 U/mL penicillin, and 100 μg/mL streptomycin). Following the incubation, the plates were washed with PBS to remove the residual non-adherent red blood cells. The resulting cells, i.e., stromal vascular fraction (SVF) containing ADSCs, were then cultured at 37° C., 5% $CO_2$ in a DMEM/F-12 culture media containing 10% FBS. The adherent cells were maintained in culture, and the media were changed every 2 days. Upon reaching an 80% confluence, the cells were digested with 0.25% trypsin/ethylenediaminetetraacetic acid at 37° C., centrifuged and resuspended DMEM/F-12 culture media. Thereafter, the cell suspensions were plated in new flasks and remained in the culture. After being passaged 3 times, the cells were used for the following analysis.

The ADSCs were cultured in a 10 cm dish, and treated with valproic acid (VPA) (1 μM or 10 μM) or BP (comprising Z-BP 95%+E-BP 5%; purchased from ECHO Chemical) (100 μM or 250 μM) at different doses for 24 hours. Then, the telomerase expression level of the ADSCs was determined by a Telomerase PCR ELISA kit (Cat. No. 11854666910, Roche). In this experiment, the ADSC group is a group without being treated by BP; the positive control group is a sample with a high expression level of telomerase (a reconstitute lyophilized cell extract, provided by the ELISA kit). The negative control group is a sample with a high expression level of telomerase which was heated at 85° C. for 10 minutes to inactive the activity of the proteins. In addition, previous research has shown that VPA could increase the telomerase activity of ADSCs, and thus, VPA is used in this experiment as a control group. The results are shown in FIG. 4.

Figure 4:
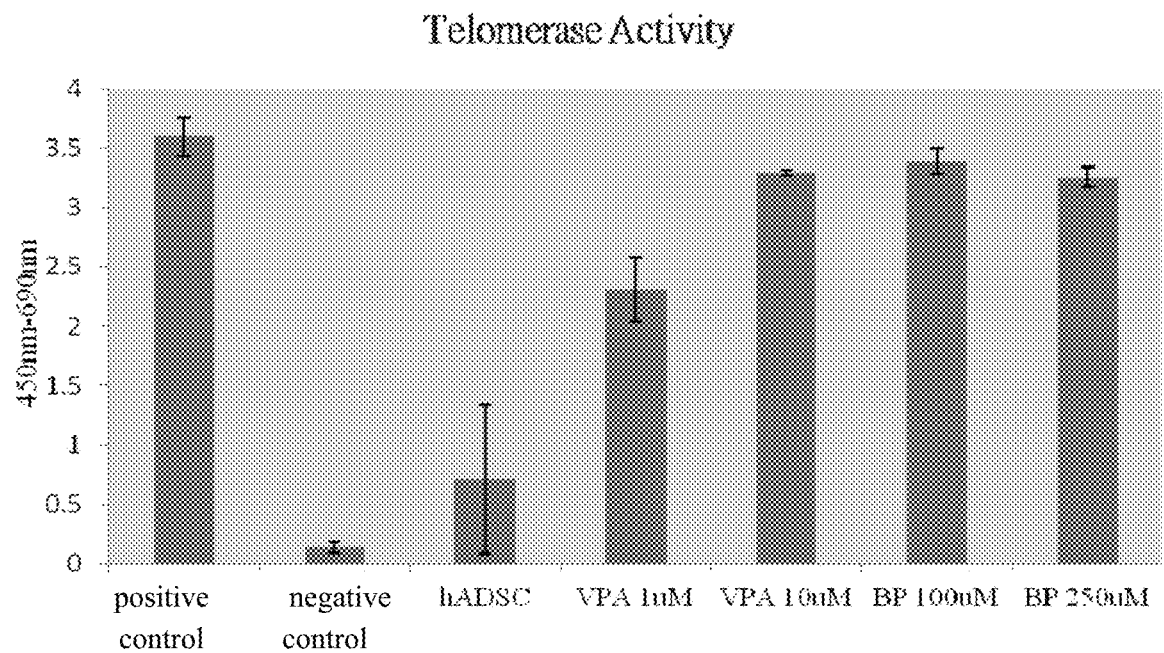
FIG. 4 is a bar diagram showing the telomerase expression levels of stem cells treated with different ingredients.

As shown in FIG. 4, the ADSCs treated with BP at a dose of 100 μM or 250 μM show a higher telomerase activity (i.e., show a higher expression level of telomerase). The above results show that BP can increase the expression level of telomerase of ADSCs, thereby prolonging the lifespan of ADSCs.

Example 5

Figure 5:
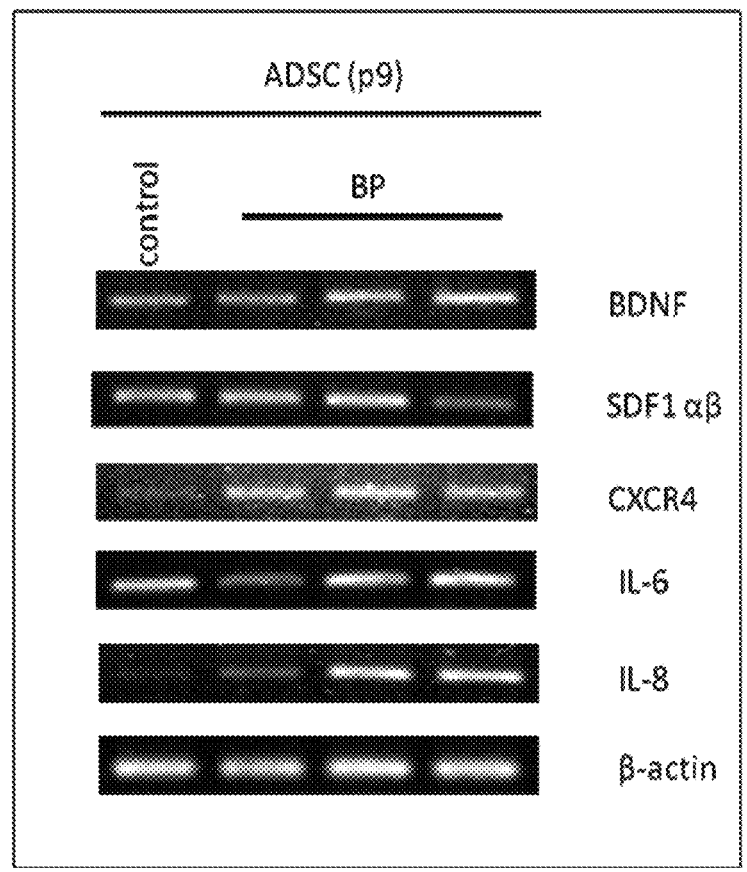
FIG. 5 is an electrophoresis picture showing the gene expression levels of BDNF, SDF1, CXCR4, IL-6 and IL-8 of stem cells treated with different ingredients.

In Vitro Study: Increase the Gene Expression Level of Neurotrophic Factor of ADSCs after Butylidenephthalide Treatment ADSCs ($2 \times 10^5$ cells/well) were cultured in a 6 well dish in a 37° C. incubator overnight. Then, the ADSCs were treated with BP (comprising Z-BP 95%+E-BP 5%; purchased from ECHO Chemical) at different doses of 10 μg/ml, 20 μg/ml, or 50 μg/ml for 12 hours. Thereafter, the gene expression levels of brain-derived neurotrophic factor (BDNF), stromal cell-derived factor-1 (SDF1), C-X-C chemokine receptor type 4 (CXCR4), interleukin 6 (IL-6), and interleukin 8 (IL-8) of the ADSCs were determined by RT-PCR. The sequences of the primers used in the RT-PCR are SEQ ID NO: 1 to SEQ ID NO: 10 as shown in Table 4 and the accompanying sequence listing. The experiment used (β-actin as a control group, and the results are shown in FIG. 5.

TABLE 4

| Primer | SEQ ID NO | Sequence (5' to 3') |
| --- | --- | --- |
| BDNF primer - Forward Sequence | SEQ ID NO: 1 | gtgtgcgaca gcattagcca gtgg |
| BDNF primer - Reverse Sequence | SEQ ID NO: 2 | cacatacatg aaactggtaa ttctcc |
| SDF1 primer - Forward Sequence | SEQ ID NO: 3 | atgaacgcca aggtcgtggt c |
| SDF1 primer - Reverse Sequence | SEQ ID NO: 4 | tcatggacct ctttcgaaat ttgttc |
| CXCR4 primer - Forward Sequence | SEQ ID NO: 5 | ggccctcaag accacagtca |
| CXCR4 primer - Reverse Sequence | SEQ ID NO: 6 | gaagttcaaa agtgaggtcg att |
| interleukin 6 primer - Forward Sequence | SEQ ID NO: 7 | tgccagcctg ctgacgaagc |
| interleukin 6 primer - Reverse Sequence | SEQ ID NO: 8 | tctgtgccca gtggacaggt |

TABLE 4-continued

| Primer | SEQ ID NO | Sequence (5' to 3') |
|---|---|---|
| interleukin 8 primer - Forward Sequence | SEQ ID NO: 9 | gctggccgtg gctctcttgg |
| interleukin 8 primer - Reverse Sequence | SEQ ID NO: 10 | tccacaaccc tctgcaccca |

As shown in FIG. 5, after the ADSCs were treated with BP (especially at the concentration of 20 µg/ml) for 12 hours, the gene expression levels of BDNF, SDF1, CXCR4 were increased. In addition, after the ADSCs were treated with BP, the gene expression levels of IL-6 and IL-8 were also increased, indicating that BP can increase the gene expression levels of cytokines to regulate the immune response, and thereby maintaining neurogenesis (see Kohman, R. A. et al., "Neurogenesis, inflammation and behavior. Brain Behav Immun, 2013. 27(1): p. 22-32," which is entirely incorporated hereinto by reference). The above results show that a combined use of BP and ADSCs can increase the expression level of BDNF, SDF 1, CXCR4, IL-6, and IL-8 of the ADSCs, and thereby, can inhibit neuron apoptosis and stimulate neurons proliferation.

Example 6

In Vivo Study: Increase the Protein Expression Level of Neurotrophic Factor of ADSCs after Butylidenephthalide Treatment SOD1-G93A transgenic mice (60-day-old) were treated with BP (comprising Z-BP 95%+E-BP 5%; purchased from ECHO Chemical) at a dosage of 500 mg/kg-body weight once daily via oral administration, transplanted with ADSCs ($2 \times 10^6$ cells/30 µl PBS) via intracerebral injection once at 60 days postnatal, and then again transplanted with ADSCs ($1 \times 10^6$ cells/150 µl PBS) via intravenous injection at 90 days postnatal. The mice were anesthetized with chloral hydrate and sacrificed at 90 days postnatal, and the spinal cords and the brain tissues were excised for immunohistochemistry analysis. The excised spinal cords and the brain tissues were postfixed overnight in 4% paraformaldehyde and subsequently cryoprotected in 30% sucrose and sectioned with a Leica cryostat to a thickness of 10 µm. Serial sections were cut from the spinal cord, frontal cortex or hippocampus of the mice, and mounted on gelatin-coated slides. To perform immunohistochemical staining, the slides were incubated in a blocking solution, and then were overnight incubated at 4° C. with an anti-human mitochondria antibody (abcan), an anti-human BDNF antibody (GeneTex), or an anti-human CXCR4 antibody (GeneTex). The results are shown in FIGS. 6A, 6B and 6C.

Figure 6A:
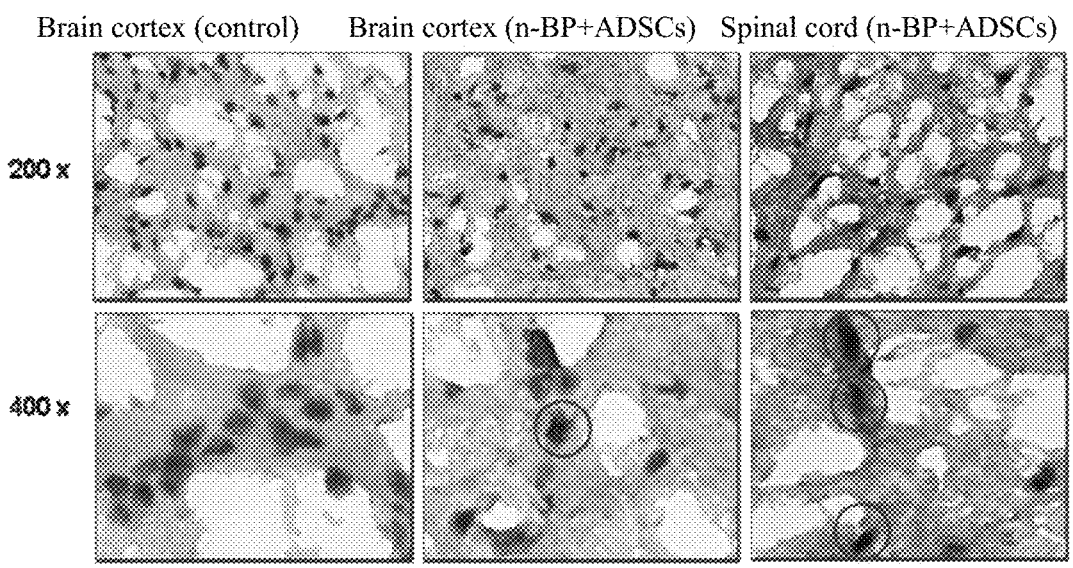
Figure 6B:
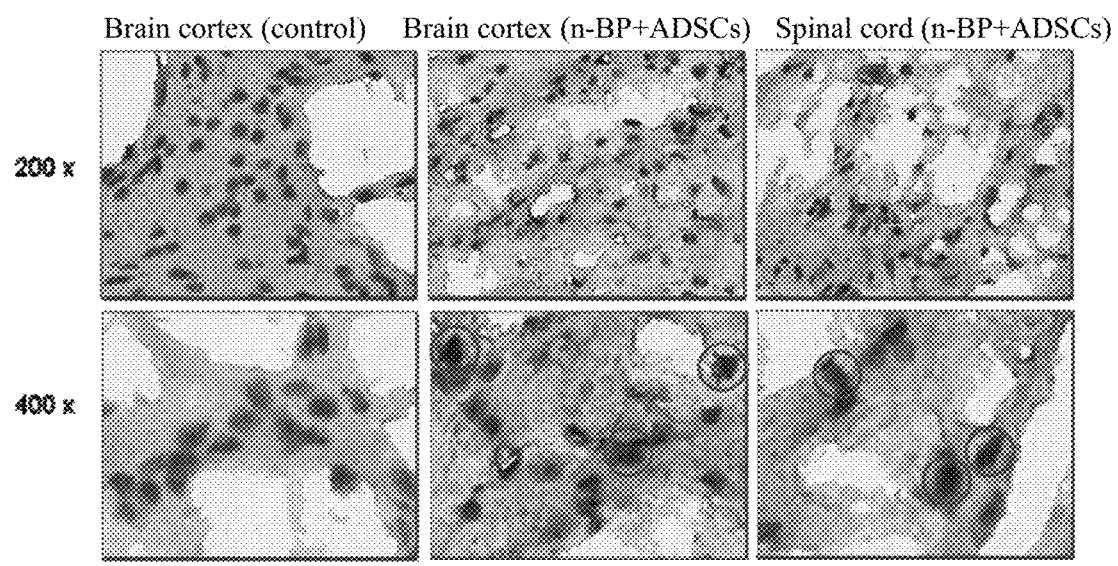
Figure 6C:
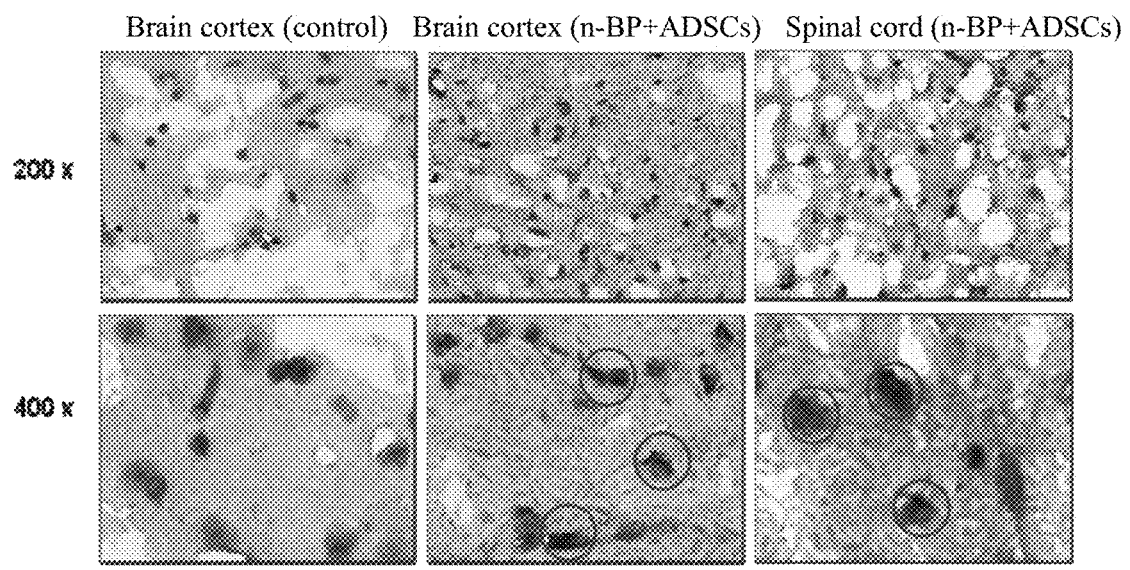

As shown in FIG. 6A, human ADSCs (see the circles marked position in FIG. 6A) can be detected in the spinal cord of the mice treated by the combination of BP and ADSCs, demonstrating that the intracerebral injected (or intravenous injected) ADSCs indeed can migrate from the brain (or the vein) to spinal cord to protect spinal motor neurons. In addition, as shown in FIGS. 6B and 6C, the mice treated by the combination of BP and ADSCs show a significant increase in the levels of human BDNF (see the circles marked position in FIG. 6B) and human CXCR4 (see the circles marked position in FIG. 6C) both in brain and spinal cord site.

The above results showed that a combined use of BP and ADSCs can increase the protein expression levels of BDNF and CXCR4 of ADSCs, and thus, can be used to inhibit neuron apoptosis and stimulate neurons proliferation.

The results in the above examples show that a combined use of a phthalide and a stem cell can increase the expression levels of telomerase, brain-derived neurotrophic factor, stromal cell-derived factor-1, and an immune regulatory factor (e.g., interleukin-6 and interleukin-8) of a stem cell in a subject to inhibit the apoptosis of motor neurons, protect motor neurons, and/or improve the proliferation of motor neurons in the subject, and thus, it can be used for treating motor neuron degenerative diseases and/or delaying the onset of motor neuron degenerative diseases.

The above examples are used to illustrate the principle and efficacy of the present invention but not used to limit to the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

What is claimed is:

1. A method for providing an increased expression of at least one of telomerase, brain-derived neurotrophic factor (BDNF), stromal cell-derived factor-1 (SDF1), CXC chemokine receptor 4 (CXCR4), and an immune regulatory factor of a stem cell in a subject, consisting of
simultaneously or separately administering to the subject an effective amount of a first composition and an effective amount of a second composition,
wherein the first composition is consisting of
(i) purified n-butylidenephthalide (BP) and
(ii) a pharmaceutically acceptable carrier, an adjuvant and/or an additive, and the second composition is consisting of
(i) an adipose stem cell and
(ii) a pharmaceutically acceptable carrier, an adjuvant and/or an additive
wherein said increased expression is increased in comparison with a corresponding expression of the stem cell in a subject without being administered with a phthalide, and
wherein the method is for at least one of treating amyotrophic lateral sclerosis and delaying the onset of amyotrophic lateral sclerosis; and
wherein the second composition is administered at an amount of about $2 \times 10^6$ cells/site via intracerebral injection and the first composition is administered in an amount of about 500 mg purified BP/kg-body weight at day 0 of treatment, and
the first composition is administered at an amount of about 500 mg purified BP/kg-body weight per day via oral administration for days 1-30 of treatment, and
the second composition is administered at an amount of about $1 \times 10^6$ cells/site via intravenous injection at day 30 of treatment.

2. The method as claimed in claim 1, wherein the method is for at least one of inhibiting the apoptosis of motor neurons, protecting motor neurons, and improving the proliferation of motor neurons in the subject.

3. The method as claimed in claim 1, wherein the first composition and the second composition are separately administered to the subject in need.

* * * * *